United States Patent
Collins

(10) Patent No.: US 6,465,206 B1
(45) Date of Patent: Oct. 15, 2002

(54) KIT FOR DETECTING TARGET MICROORGANISMS IN A CATHETER

(75) Inventor: Christopher Collins, Lancaster Gate (GB)

(73) Assignee: FAS Medical Limited, Middlesex (GB)

( * ) Notice: Subject to any disclaimer, the term of this patent is extended or adjusted under 35 U.S.C. 154(b) by 0 days.

(21) Appl. No.: 09/698,979

(22) Filed: Oct. 27, 2000

Related U.S. Application Data

(63) Continuation of application No. 08/849,101, filed as application No. PCT/GB95/02532 on Oct. 26, 1995, now abandoned.

(30) Foreign Application Priority Data

Nov. 15, 1994 (GB) .............................................. 9423020

(51) Int. Cl.[7] ................................................. C12Q 1/04
(52) U.S. Cl. ....................... 435/34; 435/309.1; 435/975
(58) Field of Search ......................... 435/34, 29, 309.1, 435/975; 604/43, 264, 280

(56) References Cited

U.S. PATENT DOCUMENTS 5,020,543 A * 6/1991 Rothenberg et al. ......... 128/760
5,407,807 A * 4/1995 Markus et al. ................. 435/34

FOREIGN PATENT DOCUMENTS

WO    WO 94/25620    10/1994

OTHER PUBLICATIONS

Rushforth J. Rapid Diagnosis of Central Venous Catheter Sepsis. Lancet vol. 342 pp. 402–403, Aug. 14, 1993.*
Cooper et al., "Rapid Diagnosis of Intravascular Catheter–Associated Infection by Direct Gram Staining of Catheter Segments", *New England J. of Medicine* 1995 1142–1147.

Johnson et al., "Vascular catheter–related sepsis:diagnosis and prevention", *J. of Hospital Infection* 1992 20:67–78.

Kiehn, T.E., "The Diagnostic Mycobacteriology Laboratory of the 1990s", *Clinical Infectious Diseases* 1993 17:S447–S454.

Maki et al., "A Semiquantitative Culture Method for Identifying Intravenous–Catheter–Related Infection", *New England J. of Medicine* 1997 296(23):1304–1309.

McGeer et al., "Improving our ability to diagnose infections associated with central venous catheters: value of Gram's staining and culture of entry site swabs", *CMAJ* 1987 137:1009–1015.

Rushforth et al., "Rapid diagnosis of central venous catheter sepsis", *The Lancet* 1993 342:402–403.

* cited by examiner

*Primary Examiner*—Ralph Gitomer
(74) *Attorney, Agent, or Firm*—Licata & Tyrrell P.C.

(57) ABSTRACT

The invention provides a method of assaying a biologically active material from an in situ catheter lumen for the presence of fibrin, a microorganism and/or debris thereof which comprises subjecting the biologically active material from the in situ catheter lumen to analysis wherein the lumen is subjected to mechanical action to dislodge the biologically active material from the wall of the catheter lumen in an amount sufficient to allow identification of a target microorganism without culturing. The invention also provides an analysis kit for this purpose.

3 Claims, No Drawings

KIT FOR DETECTING TARGET MICROORGANISMS IN A CATHETER

This application is a continuation of U.S. Ser. No. 08/849,101 filed May 13, 1997 now abanoned, which is the U.S. National Phase of PCT/GB95/02532 filed Oct. 26, 1995, which is a claims the benefit of priority of Great Britain Serial No. 9423020.8 filed Nov. 15, 1994.

The present invention relates to an assay method and particularly to an assay method for catheter related sepsis (CRS) in indwelling catheters. Although the invention is described largely relative to blood, the invention is also applicable to any body fluid such as lymph, or material removed from the catheter wall such as fibrin.

Catheter-related sepsis (CRS) is a major problem when patients are fed intravenously via a central vein. Diagnosis is based upon removal of the catheter and culture of the catheter tip. However, the majority of catheters removed on suspicion of sepsis are found to be sterile, and results of tip-cultures are often unavailable for 48 hours after removal of the catheter. There is therefore a need for a rapid and reliable test to confirm whether or not a catheter is colonised.

The acridine orange leucocyte cytospin (AOLC) test has been shown to be a sensitive test in the diagnosis of CRS in neonates, with a result in under one hour. The test has not previously been effective in adults because of the more extensive of dilution of organisms in the greater blood volume present in adults. The success of the AOLC test is dependent upon the direct detection of bacteria from a small sample (50 µl) of blood aspirated from the catheter, using ultraviolet microscopy. The high sensitivity is now thought to be due to the large concentration of bacteraemia per milliliter of blood in neonates with catheter-related sepsis. Since the relative quantitative level of bacteraemia in adults is lower, the test is not sensitive enough. When an indwelling catheter is inserted into a vein and retained in situ, a fibrin layer forms on the catheter lumen surface particularly adjacent to the tip. This fibrin is adhesive for bacteria which over time will colonise the lumen walls to create CRS. Since the bacteria are fixed, aspiration of a body fluid such as blood or lymph will not dislodge the bacteria from the walls and accordingly a technique is required to release more bacteria from the catheter into the lumen of the catheter. An endoluminal brush (Daymark Medical Industries Inc, WO94/25620) may be used for this purpose. The brush comprises nylon bristles wound tightly round the distal end of the stainless steel wire. The brush is inserted through the hub of the catheter and passed the full length of the catheter until a loss of resistance is felt as the brush exits the distal end of the catheter. The bristles are designed to remove fibrin, debris and bacteria from the surface of the catheter and hence allow detection of sepsis without removal of the catheter.

Thus, there is a release of debris and bacteria into the lumen from the surface of the catheter. The fibrin, bacteria and/or bacterial debris may then be aspirated when a body fluid (eg blood) sample is taken from the catheter. As we show below, the use of an endoluminal brush or similar means increases the quantitative level of bacteraemia in the aspirated sample from an infected catheter, so as to reach the sensitivity level of the AOLC and similar tests. Alternatively or additionally, fibrin attached to the brush may also be examined by suitable methods.

According to a first feature therefore of the present invention there is provided a method of assaying biologically active material from an in situ catheter lumen for the presence of fibrin, a microorganism and/or debris thereof which comprises subjecting the biologically active material from the in situ catheter lumen to analysis; characterised in that the lumen is subjected to mechanica action to dislodge the biologically active material from the wall of the catheter lumen in an amount sufficient to allow identification of target microorganisms without culturing. This mechanical action may be effected by means of an endoluminal brush. A particularly effective test for use in this method is a leucocyte cytospin technique or a rapid antigen test. The dislodged biologically active material may be obtained by immediate aspiration of a body fluid, such as blood, after mechanical action, or the means of applying mechanical action itself may be assayed for the presence of the biologically active material.

In the present invention we have described the use of an acridine orange leucocyte cytospin technique. However, it will be appreciated that the invention will improve the sensitivity of most appropriate assays.

The method may be assisted by concentration of the fibrin, microorganism, bacteria and bacterial debris after aspiration. This may be effected by mechanical means such as filtration or centrifugation, especially differential centrifugation at different speeds in order to separate solid components from a supernatant. The assay may be performed on the concentrated solids or may, using a rapid antigen test, be performed on the supernatant or the solid components.

Suitable staining agents may be acridine orange or Hoechst stains for example. The rapid antigen test may be effected by using one or more antibodies to give a positive response to one or more selected microorganisms.

A single assay kit may therefore include a mixed plurality of antibodies responsive to selected target microorganisms. These may include for example:

coagulase negative staphlycoccus;

*Staphylococcus aureus;*

*Escherichia coli;*

*Pseudomonas aeruginosa;*

*Streptococcus pneumoniae;* and

*Candida albinicans.*

In a further aspect of the present invention, there is provided an analysis kit for the direct detection of a target microorganism in a catheter lumen, said kit comprising:

a) assay means for the direct detection of a microorganism in an uncultured sample; and b) means to induce mechanical action within the catheter lumen to dislodge fibrin, the microorganism and/or debris thereof adherent thereto.

The assay means may comprise means for effecting an AOLC or a Hoechst staining test or a rapid antigen test, and the mechanical means to induce mechanical action may be an endoluminal brush.

The invention will now be described by way of illustration only with reference to the following clinical study:

EXAMPLE

The study was performed prospectively on 100 patients with suspected sepsis of a central venous catheter. Blood was aspirated from the catheter for an AOLC test following the decision by the managing clinical team to remove the catheter because of suspected CRS. The patients were divided equally into 2 groups.

In Group 1, the hub of the catheter was cleaned with 70% isopropyl alcohol, and one milliliter of blood was withdrawn from the central venous catheter prior to removal of the catheter.

In Group 2, after the hub was cleansed, an endoluminal brush was passed down the lumen of the catheter from the hub until the brush exited the distal end of the catheter. The brush was then retrieved from the catheter. Following removal of the brush, one milliliter of blood was withdrawn from the catheter.

Prior to removal of the catheter, the skin around the exit-site of the catheter was cleaned with 10% povidone-iodine solution. The patient was placed in a supine position. After the catheter was withdrawn, the tip was cut and placed in a dry, sterile container. The blood sample and the tip of the catheter were sent for analysis.

Microbiological Techniques

1) AOLC Test. The AOLC test was performed on a 50 µl sample from the one milliliter of blood aspirated from the catheter. The sample was mixed for 30 second with 1.2 ml of hypotonic formol saline (0.146% NaCl in 4% formalin) to lyse red blood cells and fix leucocytes. This was followed by the addition of 2.8 ml of hypertonic saline (1.168%). The solution was centrifuged at 2000 rpm for 5 minutes. After the supernatant had been decanted, the resuspended deposit was transferred to a cupule, for cytospin at 12000 rpm for 5 minutes in a Shandon II cytospin. The cytospin showered cells from the supernatant onto a slide placed on a cupule, forming a leucocyte monolayer. The slide was then stained with acridine orange (1/25000 w/v) for 30 seconds, air dried, and examined under ultra-violet microscopy. DNA-denatured bacteria can be seen as well-defined bright orange structures in, and around, the leucocytes. Viable bacteria can be seen as well defined bright green structures. A positive result was indicated by the presence of any bacteria within the sample area on the slide.

2) Culture of the Catheter Tip. Using an aseptic technique, the catheter was cut to a length of 6 cm. The external surface of the catheter was cultured using the semi-quantitative technique described by Maki (N. Eng. J Med. 296; 1305–09, 1977). The tip was rolled across 5% of the surface of the horse blood agar plate a minimum of four times. The internal surface of the catheter was cultured after sterilisation of the external surface with a cotton wool swab treated with chlorhexidine. The catheter was placed in a sterile container (bijou) with 1 ml phosphate buffered saline. The container containing the specimen was sonicated for one minute, and vortexted for 15 seconds to release any organisms from the internal surface of the catheter. Finally 10 µl and 100 µl of the fluid was transferred and spread over two blood agar plates using a sterile plastic spreader. All culture plates were examined at 24 and 48 hours, and the number of colony forming units counted and recorded. A positive result was indicated by the growth of greater than 15 colony forming units on either surface of the catheter at 48 hours.

The result of the AOLC test in both groups was compared with the cultures of the catheter tip. Statistical analysis was performed using the Chi-squared test with Yates' correction and the Mann-Whitney U test. Full informed consent was obtained from each patient, and the study was approved by the hospital ethics committee.

Results

In total, 35 of the 100 removed catheter tips showed a positive bacterial growth using the above criteria. Therefore, 65% of catheters removed on suspicion of sepsis were sterile. In Group 1, 17 out of 50 catheters were positive, while in Group 2, 18 of 50 catheters were positive. The organisms responsible for colonisation of the catheter in the two groups are shown in Table 1:

TABLE 1

| Organisms Cultured from the Catheter Tip | | |
|---|---|---|
| | Group 1 | Group 2 |
| Coagulase -ve Staphylococcus | 11 | 9 |
| Staphylococcus aureus | 2 | 3 |
| Escherichia coli | 1 | 2 |
| Pseudomonas aeruginosa | 1 | |
| Streptococcus pneumoniae | 0 | 2 |
| Candida albicans | 0 | 1 |
| Mixed bacterial growth | 2 | 1 |
| TOTAL | 17 | 18 |

In three patients from Group 1, it was not possible to aspirate blood from the catheter, hence the AOLC was not performed. The catheters from these three patients were sterile on subsequent culture. Blood was withdrawn in all patients in Group 2. The results of the AOLC tests are shown in Table 2.

TABLE 2

| Results of Cultures of the Catheter Tip and Acridine Orange Cytospin Test in the Two Groups | | | |
|---|---|---|---|
| | # | Tip positive | AOLC Positive |
| GROUP 1 (no brush) | 50 | 17 | 2 |
| GROUP 2 (brush) | 50 | 18 | 15 |

In Group 1, the AOLC was positive in only 2 patients with a positive catheter. However, when an endoluminal brush was passed prior to the aspiration of a blood sample from the catheter (Group 2), the AOLC was positive in 15 patients with a positive catheter. The AOLC was positive in significantly more patients in Group 2 ($p<0.01$). There were no false positives using the AOLC test in either group.

The number of colonies cultured from 50 µl of blood aspirated from a central venous catheter in patients with colonised catheters as shown in Table 3.

TABLE 3

Number of Colonies Cultured from 50 Microliters
Blood Aspirated from the Central Venous Catheter in
Patients
with Colonised Catheters
(2000 colonies indicates confluent growth)

| Infected Catheter No. | GROUP 1 | GROUP 2 |
|---|---|---|
| 1 | 0 | 2000 |
| 2 | 0 | 0 |
| 3 | 0 | 100 |
| 4 | 0 | 2000 |
| 5 | 0 | 2000 |
| 6 | 0 | 2000 |
| 7 | 0 | 80 |
| 8 | 0 | 2000 |
| 9 | 0 | 2000 |
| 10 | 0 | 20 |
| 11 | 0 | 60 |
| 12 | 0 | 2000 |
| 13 | 0 | 2000 |
| 14 | 2000 | 260 |
| 15 | 0 | 0 |
| 16 | 0 | 1000 |

TABLE 3-continued

Number of Colonies Cultured from 50 Microliters
Blood Aspirated from the Central Venous Catheter in
Patients
with Colonised Catheters
(2000 colonies indicates confluent growth)

| Infected Catheter No. | GROUP 1 | GROUP 2 |
|---|---|---|
| 17 | 2000 | 2000 |
| 18 | n.a. | 500 |

There was a striking contrast in the results of the AOLC in the two groups of patients. It is apparent that in Group 1, there was an insufficient release of bacteria from the surface of the catheter into the lumen. The AOLC measures a sample of 50 μl blood. Therefore, for an AOLC test to be positive, a minimum of 20 bacteria per milliliter would be required in the blood sample aspirated from the catheter. The adhesive properties of bacteria onto the surfaces of catheters are well documented and may contribute to the low sensitivity of the AOLC in patients in Group 1. In neonates with catheter-related sepsis, the quantitative levels of bacteria per milliliter of blood are significantly higher than adults, which may explain the accuracy of the AOLC in the study by Rushforth et al in The Lancet 342; 402–03 1993.

Similar results are achieved by replacing the acridic orange with a Hoechst stain at a dilution of 5 mg/liter, and prior to microscopy placing a single drop of acidic buffer on the sample slide and covering the same with a cover slip. Examination is then effected by routine fluorescence microscopy. This process gives a lower background staining.

The invention is founded on the hypothesis that if a technique was used to increase the local concentration of bacteria in the lumen of a catheter in adults, then the yield for the AOLC test would be higher. An endoluminal brush may be used to release bacteria and fibrin from the surface of the catheter into the lumen of the catheter, and into the vein around the catheter. When a sample of blood was aspirated following passage of a brush, the quantitative levels of bacteria were found to be much higher ($p<0.01$, Mann-Whitney U-test), and this resulted in the significant increase in sensitivity seen with the AOLC in Group 2.

In this study, 65% of catheters removed because of suspected infection were sterile. This emphasises the need for a reliable in situ test. This percentage is similar to other published studies. The AOLC test correctly identified all sterile catheters, although on three occasions it failed to detect a colonised catheter.

The use of the AOLC test combined with an endoluminal brush can lead to a change in clinical practice. All patients with clinical evidence of sepsis and a central venous catheter may have an AOLC test prior to investigations to find another source of sepsis. Clearly, if a positive AOLC is identified, the catheter may be removed early. Early removal of the catheter is important when catheter-related sepsis is caused by an organism of high virulence e.g. *E.coli* or *S.aureus*. A rapid result also leads to a cost-saving on other investigations, and a reduction in medical and nursing workload. On the other hand, if a suspect catheter is found to be sterile with the AOLC, a search for other sources of sepsis will be required, but the central venous catheter may remain in situ.

In conclusion the method of the invention when used with AOLC or Hoechst stain provides a rapid diagnostic test in adult patients with suspected infection related to a central venous catheter. Without the inventive method, the AOLC detected the infected catheter in only 12% of patients. However, when an endoluminal brush was used prior to the aspiration of the blood sample for analysis, the AOLC identified 83% of infected catheters. The acridine orange leucocyte cytospin test, for example, provides a rapid and sensitive test to identify infected catheters, and thus prevents the needless removal of sterile catheters.

What is claimed is:

1. An analysis kit for the direct detection of a target microorganism in a catheter lumen of an adult, said kit comprising:
   (a) an assay means for the direct detection of a microorganism in an uncultured sample; and
   (b) means to induce mechanical action within the catheter lumen to dislodge fibrin, the microorganisms and/or debris adherent to the catheter lumen.

2. A kit according to claim 1 further comprising means for effecting a mechanical separation of solids from a supernatant in an uncultured sample.

3. A kit according to either of claims 1 or 2 wherein the assay means comprises means for performing an AOLC test, a Hoechst assay, or a rapid antigen test.

* * * * *